«12» United States Patent
Yearwood et al.

«10» Patent No.: US 12,339,284 B2
«45» Date of Patent: Jun. 24, 2025

«54» ASSAY METHODS FOR IMPROVED ANALYTE DETECTION

«71» Applicant: ORASURE TECHNOLOGIES, INC., Bethlehem, PA (US)

«72» Inventors: Graham Yearwood, Bethlehem, PA (US); Michael Reed, Bethlehem, PA (US)

«73» Assignee: ORASURE TECHNOLOGIES, INC., Bethlehem, PA (US)

«*» Notice: Subject to any disclaimer, the term of this patent is extended or adjusted under 35 U.S.C. 154(b) by 473 days.

«21» Appl. No.: 16/636,795

«22» PCT Filed: Aug. 8, 2018

«86» PCT No.: PCT/US2018/045749
§ 371 (c)(1),
(2) Date: Feb. 5, 2020

«87» PCT Pub. No.: WO2019/032669
PCT Pub. Date: Feb. 14, 2019

«65» Prior Publication Data
US 2020/0371100 A1    Nov. 26, 2020

Related U.S. Application Data

«60» Provisional application No. 62/542,612, filed on Aug. 8, 2017.

«51» Int. Cl.
*G01N 33/569*   (2006.01)
*G01N 33/53*    (2006.01)
(Continued)

«52» U.S. Cl.
CPC ... *G01N 33/56988* (2013.01); *G01N 33/5302* (2013.01); *G01N 33/536* (2013.01);
(Continued)

«58» Field of Classification Search
CPC ......... G01N 33/56988; G01N 33/5302; G01N 33/536; G01N 33/558; G01N 2469/20;
(Continued)

«56» References Cited

U.S. PATENT DOCUMENTS

2006/0019406 A1   1/2006  Wei et al.
2011/0003310 A1   1/2011  Ennis et al.
(Continued)

FOREIGN PATENT DOCUMENTS

CN   103983773 A    8/2014
JP   2013513113 A   4/2013
(Continued)

OTHER PUBLICATIONS

Edisonian approach—Wikipedia (Year: 2023).*
International Search Report and Written Opinion in International Application No. PCT/US18/45749, dated Dec. 20, 2018.

*Primary Examiner* — Rebecca M Giere
«74» *Attorney, Agent, or Firm* — RAPHAEL BELLUM PLLC

«57» ABSTRACT

Disclosed herein are assay methods, lateral flow assay test strips, and devices for improved analyte detection. Analyte binding to target is performed both in solution phase and with a target immobilized on a surface, resulting in improved analyte detection.

24 Claims, 3 Drawing Sheets

Specification includes a Sequence Listing.

(51) Int. Cl.
*G01N 33/536* (2006.01)
*G01N 33/543* (2006.01)
*C07K 16/10* (2006.01)

(52) U.S. Cl.
CPC ... *G01N 33/54388* (2021.08); *C07K 16/1045* (2013.01); *G01N 2469/20* (2013.01)

(58) Field of Classification Search
CPC ....... G01N 33/56983; G01N 33/54386; G01N 33/53; C07K 16/1045; C07K 14/082; C07K 14/16; C07K 16/10
See application file for complete search history.

(56) References Cited

U.S. PATENT DOCUMENTS

| | | |
|---|---|---|
| 2012/0149124 A1 | 6/2012 | Mink et al. |
| 2012/0308444 A1 | 12/2012 | Zhu |
| 2013/0017559 A1 | 1/2013 | Babu et al. |
| 2013/0102003 A1 | 4/2013 | Gibbs |
| 2013/0130404 A1 | 5/2013 | Mehra et al. |
| 2021/0389318 A1* | 12/2021 | Reed .................. G01N 33/6854 |

FOREIGN PATENT DOCUMENTS

| | | | |
|---|---|---|---|
| WO | 9932885 A1 | 7/1999 | |
| WO | 0157522 A2 | 8/2001 | |
| WO | 2005/069002 A1 | 7/2005 | |
| WO | 2005098439 A2 | 10/2005 | |
| WO | 2006/065314 A1 | 6/2006 | |
| WO | 2006122450 A1 | 11/2006 | |
| WO | 2007/047924 A2 | 4/2007 | |
| WO | 2011069029 A2 | 6/2011 | |
| WO | WO-2011069031 A2 * | 6/2011 | ........... B01L 3/5023 |
| WO | 2013/078227 A1 | 5/2013 | |
| WO | 2015/153018 A2 | 10/2015 | |
| WO | 2017066645 A1 | 4/2017 | |

* cited by examiner

ASSAY METHODS FOR IMPROVED ANALYTE DETECTION

CROSS REFERENCE TO RELATED APPLICATIONS

This application claims priority to U.S. application 62/542,612 filed Aug. 8, 2017; the disclosure of which is incorporated herein by reference.

FIELD OF THE INVENTION

The invention relates to assay methods, lateral flow assay strips and devices for improved analyte detection.

BACKGROUND

Immunoassays are used to quantify molecules of biological interest based on the specificity and selectivity of antibody reagents generated. For point-of-care testing, immunoassays are often used in a lateral flow assay format. See, e.g., U.S. Pat. Nos. 7,192,555 and 6,303,081. Solid phase lateral flow devices incorporate a solid support strip which binds a member of an analyte-target pair. Porous materials such as nylon, nitrocellulose, cellulose acetate, glass fibers, paper, and other porous polymers are often employed as solid support strips. The sample that may contain the analyte of interest flows along the solid support across the assay. Several procedures may be utilized including the analyte or its derivative becoming bound to the immobilized target and the presence of the analyte or its derivative being detected, or the analyte or its derivative may react to form a product that is then detected.

Previous lateral flow assay strips have been used to detect various analytes using capture of analytes in the sample by orientated target molecules at a test line. For example, in a one HIV-1/2 lateral flow assay strip, a test line was prepared by conjugating Streptavidin (SA) to an anchor protein such as bovine serum albumin (BSA), and striping the conjugate at the test line location of the nitrocellulose. See e.g., U.S. Pat. Nos. 8,062,908, 7,192,555, 6,303,081, 7,541,194, and OraQuick ADVANCE® Rapid HIV-1/2 Antibody Test package insert. The SA-BSA conjugates allowed for a highly active and stable presentation of biotinylated peptides on the test line. In that lateral flow assay strip, biotin binding sites of the streptavidin were pre-loaded such that the HIV-1 and HIV-2 peptides were already on the site on SA and that captured anti-HIV antibodies in a positive patient sample as they flowed on the line. As a specimen would migrate up the strip and encounter the test line, if the specimen contained antibodies that react with the synthetic peptide antigens immobilized on the nitrocellulose membrane at the test line, a visible signal would appear, qualitatively indicating the presence of antibodies to HIV-1 and/or HIV-2 in the specimen. See id.

In typical lateral flow assay devices the specific capture of the analytes at the test zone occurs only as the liquid test sample containing analyte migrates through the test zone, and binds to its targets at a solid/liquid interface. Such devices may be improved with the addition of a binding step where the analyte binds to its target in solution, which is the subject of this invention.

SUMMARY OF THE INVENTION

This invention generally relates to assay methods, lateral flow assays strips and devices for improved analyte detection. Assay methods according to the invention detect analytes of interest from a liquid biological sample. An assay method according to the invention:

a) contacts the liquid biological sample suspected of containing an analyte with at least one ligand-target conjugate in a liquid phase, where the ligand-target conjugate binds to at least a fraction of the analyte to form a ligand-target-analyte complex;

b) contacts analyte in the biological sample and the complex from step a) with a receptor-label conjugate, to form an analyte-receptor-label complex, and a ligand-target-analyte-receptor-label complex;

c) captures the labeled complexes from step b) on a surface comprising a capture agent capable of binding ligand, where a fraction of the ligand binding sites of the capture agent are occupied by ligand-target conjugates, resulting in ligand-target-analyte-receptor-label complexes on the surface; and d) detects the ligand-target-analyte-receptor-label complexes captured on the surface. Thus, analyte binding to target is performed both with a target in a solution phase and with a target immobilized on a surface, resulting in improved analyte detection.

Assay methods of the invention may be lateral flow assays using lateral flow assay strips. Lateral flow assay strips according to the invention are designed to detect an analyte of interest from a liquid biological sample. A lateral flow strip according to the invention comprises:

a sample receiving area;

a blocker area downstream from the sample receiving area, optionally containing ligand-target conjugates;

a conjugate area downstream from the blocker area, containing label-receptor conjugates;

a test zone downstream from the conjugate area comprising immobilized capture agents capable of binding ligand, where a fraction of the ligand binding sites are occupied with ligand-target conjugates, optionally, a control zone on the lateral flow assay strip downstream from the test zone to indicate assay completion; and optionally, an absorbent pad in flow communication with the lateral flow assay strip and located downstream from the control zone.

Lateral flow devices according to the invention comprise an assay portion housing a lateral flow strips according to the invention and an opening to view the test zone and optional control zone.

DETAILED DESCRIPTION

Figure 1:
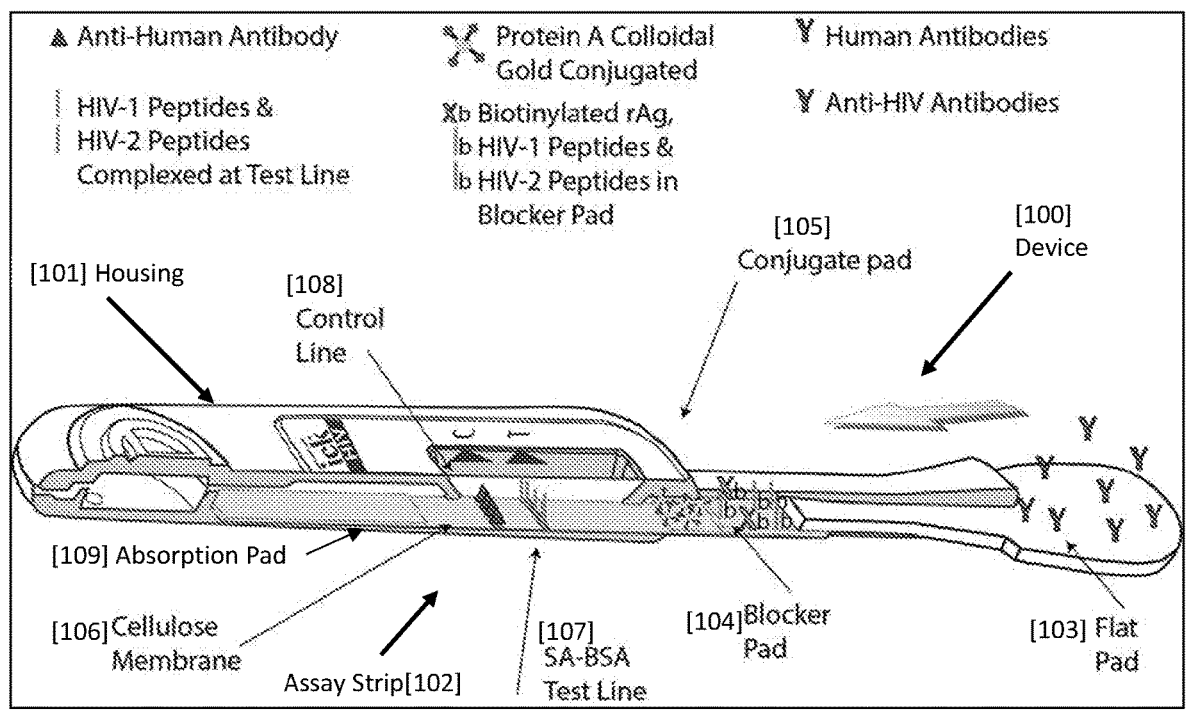
FIG. 1 shows a representative device [100] housing a lateral flow strip [102] according to the invention for improved detection of antibodies, for purposes of illustration Anti-HIV antibodies, prior to running the lateral flow assay. Anti-HIV antibodies from a biological sample are shown on the flat pad sample collector [103]. The blocker pad [104] is shown to comprise biotinylated HIV-1 peptides, biotinylated HIV-2 peptides, and biotinylated rAg peptides. The conjugate pad [105] is shown to comprise Protein A conjugated to colloidal gold. The test line [107] on the cellulose membrane [106] is shown with immobilized Bovine Serum Albumin and streptavidin, with a fraction of the biotin binding sites on streptavidin bound to biotinylated HIV-1 and biotinylated HIV-2 peptides. The control line [108] is shown with immobilized anti-human antibodies.

This invention relates to assay methods, lateral flow assays strips and devices for improved analyte detection. Improved analyte detection is achieved by combining analyte binding to target in solution phase with analyte binding to target on solid phase. An assay method for detecting an analyte in a liquid biological sample according to the invention:
 a) contacts the liquid biological sample suspected of containing an analyte with at least one ligand-target conjugate in a liquid phase, where the ligand-target conjugate binds to at least a fraction of the analyte, to form a ligand-target-analyte complex;
 b) contacts analyte in the biological sample and the complex from step a) with a receptor-label conjugate, to form an analyte-receptor-label complex, and a ligand-target-analyte-receptor-label complex;
 c) captures the labeled complexes from step b) on a surface comprising a capture agent capable of binding ligand, where a fraction of the ligand binding sites of the capture agent are occupied by ligand-target conjugates, resulting in ligand-target-analyte-receptor-label complexes on the surface; and
 d) detects the ligand-target-analyte-receptor-label complexes captured on the surface.

Assay methods according to the invention afford two mechanisms for binding the analyte to a target to bring it to a surface: i) binding of the analyte in the sample to a surface immobilized target; and ii) binding of the analyte to a ligand-target conjugate in a liquid phase, followed by capture of the analyte-target-ligand complex to a surface. In the latter, the high affinity between ligand and a capture reagent on the surface ensures that the analyte-target complexes are extracted from the solution. This combination of mechanisms provides a highly active and stable presentation of target immobilized on a surface to capture the analyte, and also allows for advantageous solution kinetics for binding in the liquid phase. By including an additional binding step in solution, assay sensitivities improve especially when slower forming complexes are given more time to form.

In an assay method of the invention the assay is performed on a lateral flow assay strip. The method further comprises contacting a lateral flow assay strip with a developer solution. Upon contact, the developer solution moves across the lateral flow assay strip. In a method of the invention, the liquid biological sample is placed in a developer solution, and the resulting developer solution comprising the biological sample moves across the assay strip to points downstream on the lateral flow assay strip. In another method of the invention, the liquid biological sample is placed on a sample receiving area of the lateral flow assay strip, and a developer solution contacts the lateral flow assay strip to facilitate the flow of the biological sample across the assay strip from the sample receiving area to points downstream.

The liquid biological sample taken for analysis using an assay method of the invention may be any liquid biological sample, such as a biological fluid, which may contain antibodies of interest. Examples of biological fluids include, but are not limited to, urine, blood, plasma, serum, oral fluids, sweat, semen, stool, sputum, cerebral spinal fluid, tears, mucus, amniotic fluid, breast milk and the like. Oral fluid is the liquid present in the oral cavity. Oral fluid is a mixture of saliva and oral mucosal transudate. Saliva is produced by the salivary glands. Oral mucosal transudate enters the mouth by crossing the buccal mucosa from the capillaries. Oral fluids contain both pathogens and antibodies. Biological fluid samples such as oral fluid, whole blood, blood plasma, and blood serum are preferred types of samples useable in an immunoassay of the invention. Each of these may be acquired using means and techniques known in the art.

Viral infection, such as infection from the HIV virus, can be detected in multiple matrices which may include liquid biological samples such as whole blood (venous or fingerstick), serum and plasma, oral fluid (e.g., saliva and oral mucosal transudate), urine, seminal fluid and breast milk from patients with clinical signs and symptoms and/or epidemiological risk factors. For example, in a method directed to measuring an oral fluid sample, a subject is handed the test device and instructed to swab the upper and lower gums once to collect saliva with the flat pad of the device. In a method of the invention directed to measuring whole blood, an appropriate volume of blood is placed onto the device by a healthcare worker. The amount of liquid biological sample to be used can vary based on the liquid biological sample and the assay format.

In an assay method of the invention, the analyte may be an antibody. Viral infection, such as infection from the HIV virus, leads to the production of anti-HIV antibodies in a patient. In a preferred assay method, the antibody is an anti-HIV antibody. The anti-HIV antibody may be an antibody against HIV-1 or HIV-2. While the assay methods of the invention are described with regard to HIV, an assay method of the invention may be used for identification, determination and/or treatment of any infection.

The assay devices, lateral flow assay strips and methods of this invention can be used for the detection (positive or negative, and/or quantification) of virtually any analyte in a biological fluid sample. Moreover, the devices, lateral flow assay strips and methods can be used to detect one or more analytes simultaneously. Such analytes may include, but are not limited to, antibodies to HIV, antibodies to HPV, antibodies to HCV, antibodies to Ebola, antibodies to Dengue, antibodies to Zika, antibodies to *Helicobacter pylori*, antibodies to hepatitis, antibodies to measles, hepatitis antigens, antibodies to terponemes, antibodies to host or infections agents, cellular markers of pathology including, but not limited to, cardiolipin, lecithin, cholesterol, lipopolysaccharide and sialic acid, antibodies to mumps, antibodies to rubella, cotinine, cocaine, benzoylecgonine, benzodiazpines, tetrahydrocannabinol, nicotine, ethanol theophylline, phenytoin, acetaminophen, lithium, diazepam, nortriptyline, secobarbital, phenobarbital, theophylline, testosterone, estradiol, 17-hydroxyprogesterone, progesterone, thyroxine, thyroid stimulating hormone, follicle stimulating hormone, luteinizing hormone, transforming growth factor alpha, epidermal growth factor, insulin-like growth factors I and II, growth hormone release inhibiting factor, IGA, sex hormone binding globulin, glucose, cholesterol, caffeine, corticosteroid-binding globulin, PSA, and DHEA-binding glycoprotein. Depending on the analyte or analytes of interest, the targets and receptors to bind to the analyte may be chosen from binding agents known in the art.

An antibody, as is known in the art, refers to a polypeptide or complex of polypeptides, substantially encoded by an immunoglobulin gene or immunoglobulin genes, or fragments thereof. The recognized immunoglobulin genes include the kappa, lambda, alpha, gamma, delta, epsilon, and mu constant regions, as well as myriad immunoglobulin variable region genes. Light chains are classified as either kappa or lambda. Heavy chains are classified as gamma, mu, alpha, delta, or epsilon, which in turn define the immunoglobulin classes (isotypes), IgG, IgM, IgA, IgD, and IgE, respectively. The constant domains of the heavy chains make up the Fc region of an antibody. The Fc portion of the antibody determines the antibody class.

Typically, an antibody is an immunoglobulin having an area on its N-terminal surface or in a cavity that specifically binds to and is thereby defined as complementary with a particular spatial and polar organization of another molecule. The antibody can be polyclonal or monoclonal. Antibodies may include a complete immunoglobulin or fragments thereof. Fragments thereof may include Fab, Fv and F(ab')2, Fab', and the like. Antibodies may also include chimeric antibodies or fragment thereof made by recombinant methods. An antigen is any compound capable of specifically binding to an antibody of interest. Specific binding of between the antigen and the antibody of interest means that the two molecules are related such that their binding with each other is capable of discriminating between binding other assay or sample components.

The target refers to a component which binds to the analyte. In assay methods of the invention the analyte specifically binds the target. In an assay method of the invention, the target may be an antigen. For example, when the analyte is an antibody, and the target may be its cognate antigen. Alternatively, when the analyte is an antigen the target may be an antibody that specifically binds the antigen. Preferably, the target is a peptide. In a preferred method of the invention, the target is selected from HIV-1 peptide, HIV-2 peptide, rAg and mixtures thereof. Anti-HIV-1 antibodies specifically bind to HIV-1 peptide, and to rAg. Anti-HIV-2 antibodies specifically bind to HIV-2 peptide. The HIV-1 and HIV-2 synthetic peptides may correspond to regions of envelope (gp120, 41) or p24 or p17 or other known proteins from the virus.

The term rAg refers to any antigenic HIV recombinant polypeptide. U.S. Pat. Nos. 5,156,949, 5,217,861, 6,428,952, 5,830,641, 5,886,319, and 6,544,728, for example, describe recombinant antigens useful for immunoassays for antibodies to HIV. The nucleotide sequence shown in SEQ ID NO 1 encodes for the recombinant antigen rAg, also known as ORA-1, HIV-1(hSOD1-HIV1gp120-41). SEQ ID NO 2 is the amino acid sequence for rAg. The mature envelope protein (Env) of HIV consists of a homotrimer of non-covalently associated gp120-gp41 heterodimers. The resulting complex protrudes from the virus surface as a spike. Surface protein gp120 interacts with human CD4, CCR5 and CXCR4, to form a P4HB/PDI-CD4-CXCR4-gp120 complex. This recombinant design of rAg expands on and includes the HIV-1 peptide sequence. The rAg antigen is recognized by anti-HIV-1 antibodies.

In methods of the invention, the target is conjugated to a ligand, forming a ligand-target conjugate. Binding of the ligand-target conjugate with the analyte results in the formation of a ligand-target-analyte complex. In step a) in methods of the invention some or all of the analyte binds to the ligand-target conjugate. If all of the analyte does not bind to the ligand-target conjugate, some of the analyte remains unbound.

The ligand serves to direct materials associated with the ligand to a surface immobilized capture reagent. For example, the ligand in the ligand-target-analyte complex serves to guide the complex to the immobilized capture reagent. In a method according to the invention, the ligand is biotin, and the ligand-target conjugate is a biotinylated peptide. Biotinylation of peptides can be performed using methods and reagents known in the art. For example, NHS-biotin can be used to label primary amine groups of peptides. The extent of biotinylation can be tested using 4'-hydroxyazobenzene-2-carboxylic acid reagent. In a method of the invention, the ligand-target conjugate is selected from biotinylated HIV-1 peptide, biotinylated HIV-2 peptide, biotinylated rAg and mixtures thereof. In preferred methods of the invention, the ligand-target-analyte complex is a complex of an anti-HIV antibody bound to a biotinylated HIV-1 peptide, a biotinylated HIV-2 peptide, or a biotinylated rAg. Biotin is capable of strong non-covalent interaction with streptavidin. In methods of the invention, streptavidin is a preferable capture reagent.

The step of contacting the liquid biological sample with a ligand-target conjugate occurs in a liquid phase. Preferably, the ligand-target conjugate is present on the lateral flow assay strip, on a blocker pad, and as liquid contacts the ligand-target conjugate, it is eluted off the blocker pad. During preparation of the lateral flow assay strip, the ligand-target conjugate may be placed on the blocker pad and dried down upon the membrane. As the analyte in the liquid phase moves across the blocker pad, the ligand target conjugate is eluted off the blocker pad into the liquid phase, is available for binding to the analyte. In a method of the invention, the ligand-target conjugate is placed on the blocker pad for liquid-phase binding. In another method of the invention, the ligand-target conjugate is added to the developer solution. In yet another method of the invention, the ligand-target conjugate is placed on the blocker pad as well as in the developer solution.

The label may be any substance which is visible itself or capable of producing a signal that is detectable by visual or instrumental means. The selection of a particular label is not critical to the invention, but the label should be capable of generating a detectable signal either by itself, or be instrumentally detectable, or be detectable in conjunction with one or more additional signal producing components, such as an enzyme/substrate signal producing system.

As is known in the art the choice of the type of label involves consideration of the analyte to be detected and the desired means of detection. Detection of the detectable label will depend on the chosen moiety or reagent, and can be done by any of the methods known in the state of the art, for example, visual inspection, ultraviolet and visible spectrophotometry, fluorimetry, radioactivity counting or the like. Typically, a visually detectable label is used. This allows for direct visual or instrumental reading of the presence or amount of an analyte in the sample without the need for additional signal producing components. Various labels known in the art and suitable for use in the methods of the invention include labels which are visible themselves or which produce signals through either chemical or physical means. Such labels can include enzymes and substrates, chromogens, catalysts, fluorescent compounds, chemiluminescent compounds, and radioactive labels. Other suitable labels known in the art include particulate labels such as colloidal metallic particles such as colloidal gold, colloidal non-metallic particles such as selenium or tellurium, dyed or colored particles such as a dyed plastic or a stained microorganism, organic polymer latex particles and liposomes, colored beads, polymer microcapsules, sacs, erythrocytes, erythrocyte ghosts, or other vesicles containing directly visible substances, and the like. U.S. Pat. No. 4,313,734 describes the use of gold sols as labels for antibodies. In a preferred assay method according to the invention, the detectable label is a metal colloidal particle, such as gold microparticles or gold nanoparticles, which can be seen by the human eye as well as instrument read. In an assay method of the invention, colloidal particles used as a detectable label have a particle size diameter of between 20 nm and 80 nm. For an instrument read assay, the concentration of the particles is measured by measuring Optical Density (OD) at a specific wavelength using a spectrophotometer. OD is then used as a measure of the total amount of labeled antigen. In an assay method according to the invention, the amount of labeled antigen should preferably be in excess of the antibody to be detected to allow for complete labeling.

The receptor-label conjugate serves to bind to the analyte in order to create a detectable complex. Depending on the analyte, the receptor may be any molecule that specifically or non-specifically binds to the analyte. In a preferred method of the invention, the receptor is Protein A. Protein A can bind to the Fc portion of several immunoglobulins. In an assay method of the invention, the receptor-label conjugate is a Protein A-gold colloid conjugate. Proteins may be attached to the colloidal gold through techniques known in the art. Protein A-gold colloid conjugates are commercially available, for example, P-6730, from Sigma Aldrich®. Other examples of receptor-label conjugates include gold conjugated antigen (Bridging assays) and secondary anti-human heavy or light chain specific gold conjugates.

In assay methods of the invention, the receptor also binds to the analyte. The receptor binds to the analyte irrespective of whether the analyte is also bound to the target. Accordingly, the receptor-label conjugate binds to the analyte to form an analyte-receptor-label complex, and the receptor-label conjugate also binds to the ligand-target-analyte complex to form a ligand-target-analyte-receptor-label complex. The step of reacting the receptor label with either the analyte or the ligand-target-analyte complex occurs in liquid phase. In methods of the invention using a lateral flow assay strip, preferably, the ligand-target conjugate is present on a conjugate pad, and as liquid contacts the receptor-label conjugate, it is eluted off the conjugate pad. During preparation of the lateral flow assay strip, the receptor-label conjugate may be placed on the conjugate pad and dried down upon the membrane. As the analyte in the liquid phase moves across the conjugate pad, the receptor-label conjugate is eluted off the conjugate pad into the liquid phase, is available for binding to the analyte and to the analyte-target-ligand complex. In a preferred method according to the invention, the ligand-target-analyte-receptor-label complex is a biotinylated peptide bound, to an antibody, bound to a Protein A conjugated colloidal gold.

In assay methods of the invention the capture reagent binds to the ligand, and serves to bring labeled complexes comprising the analyte onto a solid support for detection. Preferably the capture reagent is immobilized on a solid support. Capture reagents may be immobilized, or may be attached to other components which allow for their separation from solution. The immobilization and attachment, and placement of the capture reagent is dependent on the assay format. For example, in some assay methods of the invention, capture reagents may be immobilized on specific regions, zones, or lines on a lateral flow assay test strip, in specific regions on membranes, on solid supports of a chromatography column, or wells in microtiter plates. In other assay methods according to the invention, capture reagents may also be coated on beads or other particles to enable separation from the rest of the sample in solution. In assay methods of the invention a fraction of the ligand binding sites on the capture reagent are bound to target-ligand conjugate. In a preferred assay method of the invention, the capture reagents are located at a test line on a lateral flow assay strip, and a fraction of the capture reagents are bound to target-ligand, to enable capture of analyte, and the remaining ligand binding sites are free to capture ligand.

The affinity between the capture reagent and the ligand allows for the ligand-target-analyte-receptor-label complex to be captured by a capture reagent immobilized on a surface. Additionally, the affinity between the analyte and target allows for the analyte-receptor-label complex to bind to targets immobilized on a surface. In a preferred assay method of the invention the capture reagent is a biotin binding protein, for example, avidin, neutravidin, streptavidin, and protein conjugates thereof. Preferably, the capture reagent is streptaviding conjugated to BSA, and is immobilized on a nitrocellulose surface. In methods of the invention, biotinylated HIV-1 and HIV-2 peptides are immobilized on a surface by being bound to streptavidin-BSA immobilized on a surface, with a fraction of biotin binding sites of the streptavidin unoccupied.

A preferred assay method according to the invention detects anti-HIV-1 and anti-HIV-2 antibodies from a liquid biological sample. The method:
  a) contacts a liquid biological sample, suspected of containing anti-HIV-1 and anti-HIV-2 antibodies, with biotinylated HIV-1, HIV-2 and/or rAg peptides in a liquid phase, wherein at least a fraction of the anti-HIV-1 and anti-HIV-2 antibodies from the sample bind to the biotinylated peptides to form antibody-biotinylated peptide complexes: anti-HIV-1-biotinylated HIV-1 peptide, anti-HIV-1-biotinylated rAg peptide, and/or anti-HIV-2-biotinylated HIV-2 peptide complexes;
  b) contacts the unbound anti-HIV-1 and anti-HIV-2 antibodies in the biological sample and the complexes formed in step a), with Protein A-gold colloid conjugate to form labeled antibody complexes and labeled antibody-biotinylated peptide complexes
  c) captures the complexes from step b) with streptavidin immobilized on a surface with a fraction of the biotin binding sites on streptavidin are occupied by biotinylated HIV-1 and HIV-2 peptides
  d) detects the gold colloid-Protein A-antibody-peptide-biotin complexes from step c) captured on the surface.

A preferred method according to the invention is a lateral flow assay method. Lateral flow assays are performed on lateral flow assay strips. In a lateral flow assay method of the invention, a liquid biological sample is applied onto a lateral flow assay strip, and the presence of analytes in the biological sample is detected at a test line on the lateral flow assay strip.

A lateral flow assay strip refers to a strip utilized for lateral flow chromatography. Lateral flow (chromatography) assays typically involve the application of a liquid biological sample suspected of containing an analyte to be detected to a sample receiving area of a lateral flow (immunochromatographic) assay strip. The assay strip comprises a matrix material (e.g., paper, nitrocellulose, etc. See, e.g., U.S. Pat. No. 5,569,608) through which the test fluid and analyte suspended or dissolved therein can flow by capillary action from the sample receiving area to one or more capture zones where a visible signal, or absence of such, reveals the presence or absence of the analyte. A developer solution facilitates the flow of the sample across the lateral flow assay strip. Where the detection of the analyte utilizes an antibody or antibody fragment, the assay may be referred to as a lateral flow immunochromatography assay and the strip a lateral flow immunochromatography strip.

The lateral flow strips according to the invention afford two mechanisms of capture of the analyte of interest at the test line: i) the capture of analytes, for example antibodies, in the sample by orientated ligand-target conjugates, for example biotinylated peptides, at the test line location; and ii) by capture of ligand-target conjugates, for example biotinylated peptides, that have complexed in the mobile solution phase with analytes. The target-ligand conjugates are presented to the analyte in the liquid phase, either by addition to a developer solution or are eluted from pad component (e.g., blocker pad). In each case, it is demonstrated below that significantly (>5×) lower amounts of peptide result in a surprisingly similar reactive sample response. In lateral flow strips according to the invention, a mixture of partially occupied streptavidin-BSA (SA-BSA) leaves the test line open to a capture function for biotinylated species transported to the test line location with the sample. The test line also contains biotinylated HIV-1, HIV-2 peptides, recombinant HIV antigen(rAg) peptides, or combinations thereof, to capture anti-HIV antibodies complexed to protein-A-gold conjugates.

Binding of analyte and target in solution allows for liquid phase binding, where they are able to benefit from the test run time to allow the targets to effectively incubate with the analytes from the sample. For example, as a patient sample containing anti-HIV antibodies is transported into the device by the developer solution, which hydrates and elutes the pad components, biotinylated peptides and recombinant proteins displaying HIV epitopes can take advantage of solution kinetics and the flow time to the test line to more completely complex with anti-HIV antibodies in the sample. The high affinity biotin-streptavidin binding then ensures these complexes are extracted from the solution by the immobilized free biotin binding sites on streptavidin at the test line.

A lateral flow assay strip for detecting an analyte from a liquid biological sample according to the invention comprises:
  a sample receiving area;
  a blocker area downstream from the sample receiving area, optionally containing ligand-target conjugates;
  a conjugate area downstream from the blocker area, containing label-receptor conjugates;
  a test zone downstream from the conjugate area comprising immobilized capture agents capable of binding ligand, wherein a fraction of the ligand binding sites are occupied with ligand-target conjugates,
  optionally, a control zone on the lateral flow assay strip downstream from the test zone to indicate assay completion; and
  optionally, an absorbent pad in flow communication with the lateral flow assay strip and located downstream from the control zone. Preferably, a lateral flow strip of the invention is designed with a liquid sample flow direction consecutively through a sample receiving area, a blocker area, a conjugate area, a test line, a control line and an absorbent pad. The absorbent pad assists in promoting capillary action and fluid flow one-way through the membrane of the strip, and pulls the liquid containing the analyte along the membrane from one end of the strip to the other.

Figure 2:
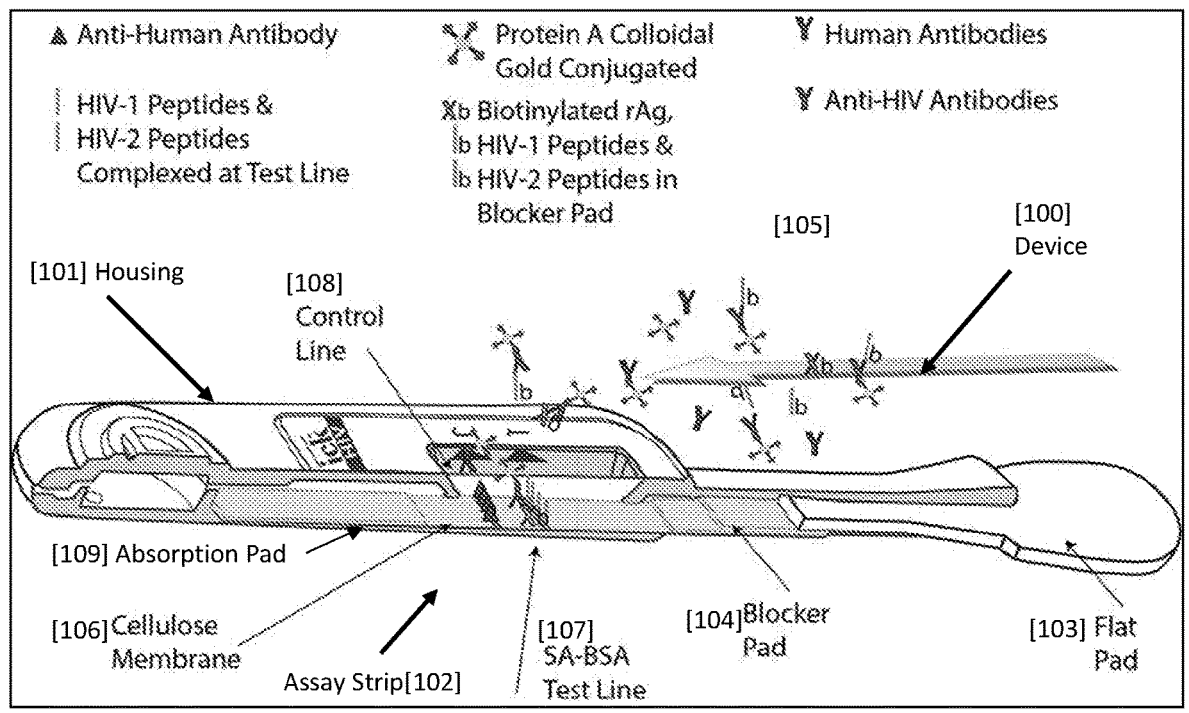
FIG. 2 shows a representative device [100] housing a lateral flow strip [102] according to the invention for improved detection of Anti-HIV antibodies during the lateral flow assay, as the sample reaches the test line [107]. As the sample containing Anti-HIV antibodies moves to the blocker pad [104], a fraction of the Anti-HIV antibodies bind to biotinylated HIV-1 peptides, biotinylated HIV-2 peptides, and biotinylated rAg peptides. As the sample moves to the conjugate pad [105], Anti-HIV antibodies bound to biotinylated further bind to Protein A—colloidal gold conjugates. Unbound Anti-HIV antibodies also bind to Protein A—colloidal gold conjugates.
Figure 3:
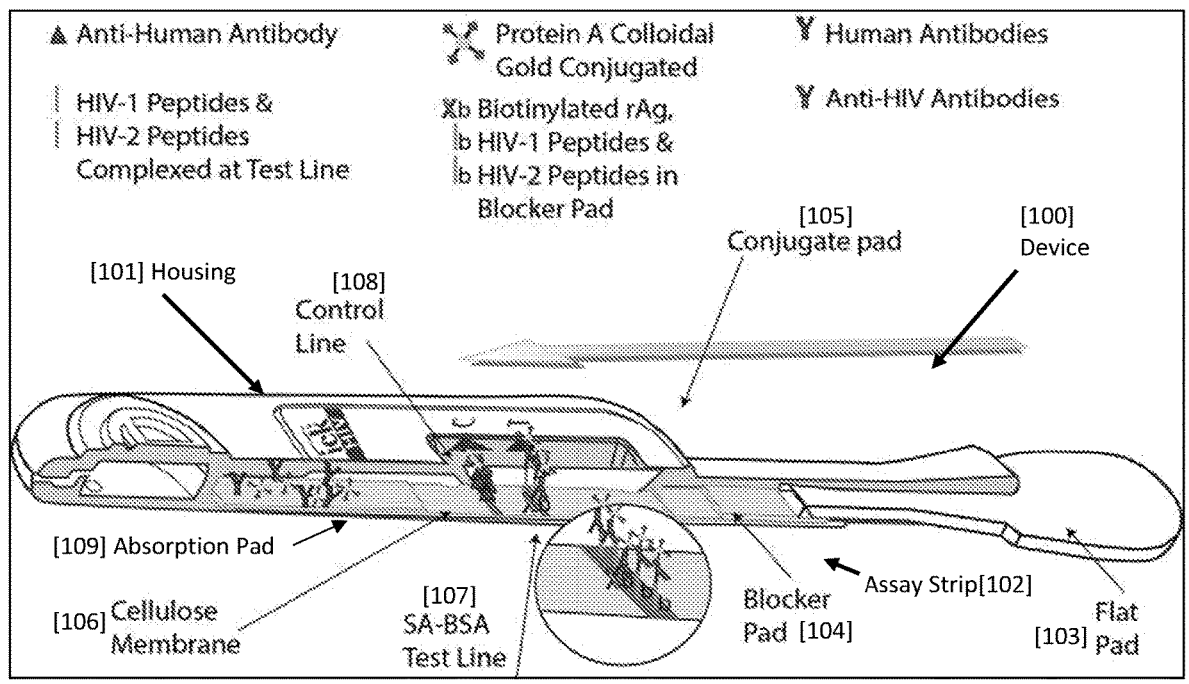
FIG. 3 shows a representative device [100] housing a lateral flow strip [102] according to the invention for improved detection of Anti-HIV antibodies after running the lateral flow assay as the sample flows past the control line [108] and into the absorbent pad [109]. At the test line [107], biotinylated HIV-1 and biotinylated HIV-2 peptides complexed with streptavidin capture anti-HIV antibodies complexed with Protein A-colloidal gold conjugates. Also at the test line [107], streptavidin captures the complex of biotinylated peptides complexed with Anti-HIV antibody complexed with Protein A-colloidal gold conjugates. At the control line [108], anti-human antibodies capture any human antibodies in the biological sample. Anti-HIV antibodies complexed with Protein A-colloidal gold conjugate are visible as they bind to the anti-human antibodies on the control line [108].

FIG. 1-3 illustrate a lateral flow device according to the invention. The lateral flow device [100] has a housing [101]. The device [100] contains a lateral flow assay strip [102] having a flat pad [103] partially exposed outside the housing [101] which is in flow communication with a blocker pad [104] and a conjugate pad [105] disposed on a cellulose membrane [106] having a test line [107] as its capture zone, and a control line [108] as its optional control zone. The cellulose membrane 106 is in flow communication with an optional absorbent pad [109]. The direction of flow is indicated by the arrow. A drop of sample from a subject is applied to the flat pad [103]. The sample is wicked across the lateral flow strip [102] within the device housing [101], and flows from the flat pad [103] to a conjugate pad [105] and across the cellulose membrane [106]. As depicted here, the flat pad [103] acts as a wick to deliver a liquid biological to the blocker pad [104].

The liquid biological sample analyzed using a lateral flow strip of the invention may be any liquid biological sample, such as a biological fluid, which may contain antibodies of interest. Examples of biological fluids include, but are not limited to, urine, blood, plasma, serum, oral fluids, sweat, semen, stool, sputum, cerebral spinal fluid, tears, mucus, amniotic fluid, breast milk and the like. Oral fluid is the liquid present in the oral cavity. Oral fluid is a mixture of saliva and oral mucosal transudate. Saliva is produced by the salivary glands. Oral mucosal transudate enters the mouth by crossing the buccal mucosa from the capillaries. Oral fluids contain both pathogens and antibodies. Biological fluid samples such as oral fluids, whole blood, blood plasma, and blood serum are preferred types of samples useable in an immunoassay of the invention. Each of these may be acquired using means and techniques known in the art. The amount of liquid biological sample to be used can vary based on the liquid biological sample, as known in the art.

A lateral flow strip of the invention may be used to detect an analyte that is an antibody. Preferably, the antibody is an anti-HIV antibody. The anti-HIV antibody may be an antibody against HIV-1 or HIV-2. While the lateral flow strips of the invention are described with regard to HIV, lateral flow strip of the invention may be used for identification, determination and/or treatment of any infection.

A "sample receiving area" of the lateral flow assay strip refers to the area of the lateral flow assay test strip to which a sample is first applied. In addition to receiving the sample, the functions of the sample receiving area may include, for example: pH control/modification and/or specific gravity control/modification of the sample applied, removal or alteration of components of the sample which may interfere or cause non-specific binding in the assay, or to direct and control sample flow to the test region. The filtering aspect, if present, allows an analyte of interest to migrate through or across a lateral flow assay test strip in a controlled fashion with few, if any, interfering substances. The filtering aspect, if present, often provides for a test having a higher probability of success and accuracy. In a lateral flow assay test strip of the invention, the sample receiving area may also incorporate reagents useful to avoid cross-reactivity with non-target analytes that may exist in a liquid biological sample and/or to condition the sample; depending on the particular embodiment, these reagents may include anti-RBC reagents, Tris-based buffers, EDTA, among others. When the use of whole blood is contemplated, anti-RBC reagents are frequently utilized. In yet another assay strip of the invention, the sample receiving area may incorporate other reagents such as ancillary specific binding members, fluid sample pretreatment reagents, and signal producing reagents. In a lateral flow assay device according to the invention, the flat pad [103] serves as a sample receiving area.

In some lateral flow assay strips according to the invention, the sample receiving area may be a sample pad and may be made from any material capable of receiving the liquid biological sample and absorbing the liquid sample when applied and of passing the liquid sample to the blocker pad. The pad in the sample receiving area can be constructed to act as a filter for cellular components, hormones, particulate, and other certain substances that may occur in the fluid sample. Sample pad materials suitable for use in assay strips of the invention also include those application pad materials disclosed in U.S. Pat. No. 5,075,078, incorporated herein by reference. Suitable materials for the sample application area include, but are not limited to, hydrophilic polyethylene materials or pads, acrylic fiber, glass fiber, filter paper or pads, desiccated paper, paper pulp, fabric, and the like.

The sample receiving area may be comprised of a sample application member (e.g., a wick or a flat pad). The sample receiving zone can comprise a sample application pad as well as a sample application member. Often the sample application member is comprised of a material that readily absorbs any of a variety of fluid samples contemplated herein, and remains robust in physical form. Frequently, the sample application member is comprised of a material such as white bonded polyester fiber. The sample application member may also be treated with a hydrophilic finishing agent. Moreover, the sample application member is positioned in fluid-flow contact with the blocking pad of the lateral flow assay strip. This fluid flow contact can comprise an overlapping, abutting or interlaced type of contact. Often the sample application member, if present, may contain similar reagents and be comprised of similar materials to those utilized in exemplary sample application pads. The liquid biological sample may be applied to the flat pad [103] directly. For example, the flat pad [103] may be inserted in the mouth of a subject, and be used as a collection pad for oral fluids. Other fluids, for example blood or serum may be directly placed on the flat pad [103]. The liquid biological sample may also be diluted in a developer solution in a vial, and the flat pad [103] may be placed in the vial.

The assay strips of this invention include a blocker area which contains at least one target-ligand conjugate. In a lateral flow strip of the invention, the blocker area is a blocker pad. As shown in FIG. 1, the blocker pad [104] is downstream of the flat pad [103]. As known in the art, a blocker pad contains reagents to ensure minimal reactivity within the device to nonspecific or interfering substances that are present in various sample matrices. A blocker pad can be composed of a wide variety of materials as long as they do not impede flow of oral fluid downstream to the lateral flow assay test strip. Such materials include, but are not limited to, paper, cellulose, nitrocellulose, polyester, glass fiber, and the like. Materials may be selected to reduce or eliminate backflow of reagents or oral fluid from the chromatographic test strip to the capillary matrix. Buffering reagents and salts present may be present in the blocker pad to help adjust the pH and ionic strength for complexing the target with analyte. A blocker pad can be impregnated with buffers to adjust the sample pH of the liquid biological sample as it flows and for compatibility with the lateral flow assay. A blocker pad can also include one or more blocking reagents that reduce non-specific binding of an analyte and/or reagents of the assay and thereby reduce the occurrence of false positives. Exemplary blocking reagents include, but are not limited to, bovine serum albumin (BSA), methylated BSA, casein, nonfat dry milk, deoxycholate, and n-lauroyl sarcosine. The blocking solution may also contain surfactants, preservatives and other reagents to enhance flow across the test strip, improve assay results and protect sample integrity. Typically, a blocker pad is made by applying an appropriate volume of blocking solution onto the pad and drying before positioning it on the lateral flow assay strip.

The blocker pad of a lateral flow assay test strip of the invention optionally serves to maintain ligand-target conjugate reagents in a stable state and to facilitate their rapid and effective solubilization, mobilization and specific reaction with analytes of interest potentially present in the liquid biological sample. FIG. 1-3 illustrate a device housing [100] a lateral flow strip according to the invention in which the blocker pad also contains the target-ligand conjugate. As the developer solution along with biological sample flows across the lateral flow strip [102], target-ligand conjugate is eluted off the blocker pad [104] and at least a fraction of the analyte present in the biological sample binds to the target-ligand conjugate in the liquid phase. In a lateral flow strip of the invention, the target is an antigen. Preferably, the antigen is selected from the group consisting of HIV-1 peptide, HIV-2 peptide, rAg and mixtures thereof, and the ligand is biotin. Accordingly, preferred target-ligand conjugates on the blocker pad include biotinylated HIV-1 peptide, biotinylated HIV-2 peptide, biotinylated rAg, or mixtures thereof.

The conjugate area of a lateral flow assay test strip serves to maintain label reagents and control reagents in a stable state and to facilitate their rapid and effective solubilization, mobilization and specific reaction with analytes of interest potentially present in the liquid biological sample. In a lateral flow assay test strip according to the invention, the conjugate area can be a conjugate pad. A conjugate pad is positioned on a lateral flow assay test strip such that the liquid biological sample must pass across or though the conjugate pad in order to migrate to the test zone or line. Alternatively, a conjugate area can be woven into the lateral flow assay test strip or can be placed in-line, in the same place, as the lateral flow assay test strip. As with a blocker pad, a conjugate pad can be fashioned out of any convenient material (e.g., nitrocellulose) that is compatible with the assay and that does not substantially impede flow of the oral fluid and reagents. Conjugate pad materials suitable for use by the present invention include those chromatographic materials disclosed in U.S. Pat. No. 5,075,078, which is herein incorporated by reference.

In a lateral flow assay test strip according to the invention, the conjugate pad carries the receptor-label conjugate as well as release and stabilization agents to allow for detection of antigen at a test zone or line. Depending on the analyte, the receptor may be any molecule that specifically or non-specifically binds to the analyte. In a preferred lateral flow assay strip of the invention, the receptor is Protein A, and the label is a gold colloid. As the developer solution along with the biological sample flows across the lateral flow strip, receptor-label conjugate is eluted off the conjugate pad, and the receptor-label binds to analyte or to the analyte-target-ligand complex.

Assay strips according to the invention comprise a matrix material (e.g., paper, nitrocellulose, etc., see, e.g., U.S. Pat. No. 5,569,608) across which the test fluid and analyte suspended or dissolved therein can flow by capillary action. Matrix materials can include, but are not limited to, natural, synthetic, or naturally occurring materials that are synthetically modified, such as polysaccharides (for example, cellulose materials such as paper and cellulose derivatives as cellulose acetate and nitrocellulose); polyether sulfone; nylon; silica; inorganic materials, such as deactivated alumina, diatomaceous earth, magnesium sulfate, or other inorganic finely divided material uniformly dispersed in a porous polymer matrix such as vinyl chloride, vinyl chloride-propylene copolymer, and vinyl chloride-vinyl acetate copolymer; cloth, both naturally occurring (for example, cotton) and synthetic (for example, rayon); porous gels, such as silica gel, agarose, dextran, and gelatin; polymeric films, such as polyacrylamide, and the like. In a preferred assay strip of the invention, the matrix material is a nitrocellulose membrane. Different types of commercially available nitrocellulose membranes (e.g., Millipore, HF90, GE FF120, Sartorius) possess different absorbent capacity and capillary flow.

In a lateral flow assay test strip of the invention, the matrix material may be adhered to a laminate backing. The backing may be a plastic material, such as e.g. Mylar or PVC or polystyrene. In preparing assay strips, the matrix material may be laminated onto a plastic card using techniques known in the art. Nitrocellulose membranes with laminate backings are commercially available.

In a lateral flow assay test strip according to the invention, a test zone or test line, downstream from the conjugate area, serves to indicate the presence of analytes. The test zone or line includes capture reagents and ligand-target conjugate molecules immobilized on the lateral flow assay strip. The capture reagent may be any compound capable of specifically binding to the ligand. In a preferred lateral flow assay test strip according to the invention, the immobilized capture reagent is streptavidin. The test line also includes immobilized targets. The targets may be biotinylated, and bound to streptavidin, and thereby immobilized on the test zone. Accordingly, in a lateral flow assay strip of the invention the test line comprises streptavidin molecules immobilized on the strip where a fraction of the biotin binding sites are occupied by biotinylated targets. In a preferred lateral flow strip of the invention, the test zone includes, prior to any addition of sample, streptavidin with available biotin binding sites, and streptavidin bound to biotinylated HIV-1 peptide, biotinylated HIV-2 peptide, biotinylated rAg, or mixtures thereof. Attachment of proteins, such as streptavidin onto nitrocellulose is known in the art. In a preferred lateral flow assay strip of the invention, streptavidin-BSA is placed on the nitrocellulose at the test line. As the sample moves to the test line, biotinylated targets, biotinylated target-analyte complexes, and biotinylated target-analyte-receptor-label complexes will bind to streptavidin on the test zone, and analytes, and analyte-receptor-label complexes will bind to the immobilized targets on the test line. The presence of analyte is detected through visualization of the label at the test line.

A control zone or control line may also be placed on the lateral flow assay test strip downstream from the test zone. The control line, binds labeled antigen not captured in the test zone. A positive control line indicates that the device has functioned appropriately. In a lateral flow assay strip according to the invention testing for antibodies in the liquid biological sample from a human, the control line on the nitrocellulose membrane is striped with anti-human antibodies.

An adsorbent pad may be present downstream of the control line in a lateral flow assay test device. The absorbent pad serves not only as the end reservoir for device fluid but may also draw the fluid across the lateral flow assay test strip. Absorbent pads should have sufficient wicking characteristics to prevent backflow of liquid upstream on the assay strip. The absorbent pad may be made of materials known in the art.

Assay test strips according to the invention may be prepared and assembled using techniques known in the art, as discussed above. Assay test strips according to the invention may be in a housing. An assay device according to the invention, comprises a housing having an opening or window to view one or more capture zones and control zones.

A lateral flow assay method according to the invention uses a developer solution. One embodiment of the invention is a kit comprising a lateral flow assay strip of the invention and a developer solution. A developer solution facilitates the capillary flow of the biological sample into the device and onto the assay strip. In an assay method of the invention oral fluid may be collected and serve as the biological sample. For oral fluid collection, the sample application member or collection pad of the device, is first used to receive or collected a biological liquid sample. For example a collection pad of a device may be used to collect an oral fluid sample from a subject's mouth, and then is placed in a vial of developer solution. The collection pad wicks up the developer solution carrying along with it the oral fluid sample for the lateral flow assay test. For other biological samples, such as whole blood, serum or plasma collection, the sample is added directly into a vial containing developer solution or onto the collection pad, and the collection pad is subsequently placed in the developer vial to flow through the lateral flow assay test and thereby transport the sample. In a particular assay method according to the invention, whole blood is directly applied to the sample application area, for example, a drop of whole blood drop (5 μL to 50 μL) obtained from a fingerstick or venipuncture or needle without any type of prior dilution or treatment. A developer solution is typically an aqueous solution of surfactants, salts, preservatives, buffering agents, etc. as known in the art. Buffer system such as phosphate, Tris-Cl borate, bicarbonate, etc., may be used. Surfactants such as Tween 20, Triton X-100 or other non-ionic detergents may be used. Preservatives, including anti-microbial and anti-fungal substances, such as, e.g., sodium azides may be used in the developer solution. The amount of developer solution used should be sufficient to transport the sample but not so much as to swamp the assay or dilute the results so they cannot be determined.

EXAMPLES

Example 1

A lateral flow assay device was prepared. Striped nitrocellulose, a blocker pad, a conjugate pad and an adsorbent pad were assembled on an assay card backing.

- Striped Nitrocellulose: FF120 nitrocellulose was line striped with solutions of anti-human antibody (F(ab')2, Goat anti-Human IgG) at the control line and SA-BSA, partially pre-complexed with biotinylated HIV-1 and HIV-2 peptides at the test line.
- Blocker Pad: The biotinylated rAg was added to the blocker pad solution along with biotinylated HIV-1 and HIV-2. The blocker pad was treated with a common blocker base buffer and biotinylated HIV-1 and HIV-2 peptides and biotinylated rAg.
- Conjugate Pad: Colloid gold was formulated using the citrate reduction process (Turkevich method), passively coated with protein A. The conjugate pad was made by spraying formulated gold conjugate solution onto the conjugate pad material. This conjugate pad was allowed to dry appropriately before being positioned immediately above the blocker pad on the assay card.

Once all major components of the assay card were available (blocker pad, conjugate pad, nitrocellulose, laminate backing, absorbent pad), the materials were assembled into an assay card on a laminate backing card. Assay cards were cut into assay strips and the assay strip was set in the device housing base and a collection pad was placed on top of the assay strip in the device housing base. The device housing top was pressed together to engage the pins in the base with the sockets in the top to complete the assembly. The assembled device was sealed upon assembly.

The assay method was performed by collection of the biological sample, insertion of the sample into developer buffer, followed by the insertion of the test device and interpretation of the assay results after approximately 20 to 40 min. An oral fluid specimen was collected using the flat sample collection pad of the test device, followed by the insertion of the test device into the vial of developer solution. The developer solution facilitated the flow of the specimen into the device and onto the lateral flow assay test strip.

Example 2

Seroconversion panels: Table 1 is a summary of the performance of the seroconversion panels from the package insert for the OraQuick ADVANCE® Rapid HIV-1/2 Antibody Test. Table 2 is a summary of seroconversion panels tested with a lateral flow assay device according to the invention.

TABLE 1

Performance in Seroconversion Panels with the OraQuick ADVANCE ® Rapid HIV-1/2 Antibody Test device

| Number of Panels | Number of Concordant Results | Number detected Earlier by device | Number detected earlier by EIA | Average Days device | Average Days EIA | Delay Days |
|---|---|---|---|---|---|---|
| 23 | 7 | 3 | 13 | 36.46 | 34.99 | 1.48 (95% CI −0.1 to 3.1) |

TABLE 2

Performance in Seroconversion Panels with a test device according to the invention

| Number of Panels | Number of Concordant Results | Number detected Earlier by device | Number detected earlier by EIA | Average Days device[a] | Average Days EIA[a] | Delay Days[b] |
|---|---|---|---|---|---|---|
| 21 | 11 | 4 | 6 | 36.19 | 35.95 | 0.24 (95% CI: −1.34 to 1.81) |

[a]Calculated using MiniTab ® Statistical Software.
[b]Delay Days are equivalent to the mean differential sensitivity between the device and the U.S. FDA-approved EIA.

The package insert for the currently approved test device indicates a delay of 1.48 days between when OraQuick detects antibodies to HIV and when EIA (ELISA Immunoassay) detects the antibodies, while the device according to the invention indicates a delay of 0.24 days, essentially equivalent sensitivity to laboratory based antibody tests. HIV is transmitted primarily through sexual contact, contact with infected blood, blood products or human tissue and from mother to child (Smith D K, Grohskopf L A, Black R J, et al, MMWR Recomm. Rep. 54:1-20 2005; Kourtis A P, Lee F K, Abrams E J, et al., Lancet Infect Dis. 6:726-732 2006. Globally, most HIV transmission occurs as a result of unprotected sexual contact. HIV transmission rates per coital act with an infected partner are estimated to be relatively low, but the risk can be increased substantially if the viral load in the source patient is high (e.g. during acute HIV infection: Cohen M S, Pilcher C D, J. Infect. Dis. 191:1391-1393 2005). Enhanced sensitivity is important for detection for such individuals.

Example 3

The amount of antigen used in the assay method was evaluated based on whether it was striped, eluted off a pad, or added to the developer solution. For each condition below, 3 μL of samples (PM2=HIV-1 plasma sample; PM6=HIV-2 plasma sample; PM10=HIV-negative plasma; 9012-8—seroconversion plasma sample) was added to the liquid phase (Developer) and the device placed in this mixture to initiate the test.

In Condition 1, as shown in Table 3, peptides were striped on the nitrocellulose. The per-device level of each peptide was estimated at 82.1 ng of biotinylated HIV-1 and 33.2 ng of biotinylated HIV-2.

TABLE 3

| Nitro/Condition | Striped Modified avidin complexed with HIV peptides/Condition 1 |
|---|---|
| Developer | Developer A (750 μL) |
| Blocker pad | HIV blocker |
| Sample | Test Line Response |
| PM 2 | Reactive |
| PM 6 | Reactive |

In Condition 2, shown in Table 4, peptides were added to the developer solution. There were no biotinylated peptides pre-bound on the test line. The per-device level of each peptide was estimated at 13.3 ng of biotinylated HIV-1 and 5.3 ng of biotinylated HIV-2.

TABLE 4

| Nitro/Condition | Striped biotin binding protein/Condition 2 |
|---|---|
| Developer | Developer A (750 μL) spiked with 100 ng HIV-1 and 40 ng HIV-2 biotinylated peptides |
| Blocker pad | HIV blocker |
| Sample | Test Line Response |
| PM 2 | Reactive |
| PM 6 | Reactive |
| PM 10 | Non-Reactive |

In Condition 3, shown in Table 5, the peptides were added to the blocker pad. The per-device level of each peptide is estimated at 14.4 ng of biotinylated HIV-1 and 5.8 ng of biotinylated HIV-2.

TABLE 5

| Nitro/Condition | Striped biotin binding protein/Condition 3 |
|---|---|
| Developer | Developer A (750 μL) |
| Blocker pad | Biotinylated HIV-1: 1800 ng/mL Biotinylated HIV-2: 720 ng/mL |
| Sample | Test Line Response |
| PM 2 | Reactive |
| PM 6 | Reactive |
| PM 10 | Non-Reactive |

In Conditions 2 and 3, the biotinylated peptides were present in the liquid phase (developer solution) or eluted off from the pad component, and in each case, it was demonstrated that significantly (>5×) lower amounts of peptide result in a surprisingly similar reactive sample response relative to when the peptide was striped on the test line (Condition 1). Exploiting the liquid phase kinetics of the lateral flow platform dramatically reduced the amount of immunoreactive material required to secure a device reactive response.

Example 5

Expanding the epitope coverage by use of a recombinant protein also benefited from the solution phase versus solid phase presentation. This was demonstrated through use of a Zeptomatrix seroconversion sample (9012-8), a sample that has been characterized as p24 and HIV EIA positive and is representative of an acute infection.

In Condition 4, rAg was striped on the nitrocellulose strip. The per-device level of the recombinant antigen (rAg) was estimated at 189 ng of biotinylated rAg.

TABLE 6

| Nitro/Condition | 1 mg/mL rAg/Condition 4 |
|---|---|
| Developer | Developer A (750 μL) |
| Blocker pad | HIV blocker |
| Sample | Test Line Response |
| PM2 | Reactive |
| 9012-8 | Non-Reactive |

In Condition 5, rAg was added to the developer buffer. BBP was striped on the nitrocellulose, unbound with any biotinylated peptides. The per-device level of the rAg was estimated at 50 ng of biotinylated HIV-1 rAg. PM2 and seroconversion sample 9012-8 were reactive on the device under this condition. By comparison, when biotinylated peptide was added to the developer alone (Condition 6), 9012-8 was not reactive (Table 8).

TABLE 7

| Nitro/Condition | Striped biotin binding protein/Condition 5 |
|---|---|
| Developer | Developer A (750 μL) spiked with 50 ng biotinylated rAg |
| Blocker Pad | HIV blocker |
| Sample | Test Line Response |
| PM2 | Reactive |
| 9012-8 | Reactive |

TABLE 8

| Nitro/Condition | Striped biotin binding protein (BBP)/Condition 6 |
|---|---|
| Developer | Developer A (750 μL) spiked with 50 ng biotinylated HIV-1 peptide |
| Blocker pad | HIV blocker |
| Sample | Test Line Response |
| PM2 | Reactive |
| 9012-8 | Non-Reactive |

Example 6

There is a surprising advantage to having a fraction of the peptides striped on the nitrocellulose. Shown below in Table 9 are a series of seroconversion samples, samples 9012-7, 9077-14, 965-4, 109-7, and 204-3, that are HIV EIA positive where reactivity is absent when the peptides are only present in the blocker pad but not pre-bound on the test line. As the proportion of peptides on the nitrocellulose is increased, reactivity in these samples is gained, while HIV negative samples remain negative.

TABLE 9

| Nitrocellulose | Striped BBP | Striped BBP with 25% Peptides | Striped BBP with 50% Peptides |
|---|---|---|---|
| Developer | | HIV developer | |
| Blocker pad | | HIV blocker with biotinylated HIV peptides and biotinylated rAg | |
| Sample | | Test Line Response | |
| PM 2 | Reactive | Reactive | Reactive |
| PM 6 | Reactive | Reactive | Reactive |
| PM 10 | Non-Reactive | Non-Reactive | Non-Reactive |
| 9012-7 | Reactive | Reactive | Reactive |
| 9077-14 | Non-Reactive | Reactive | Reactive |
| 965-4 | Non-Reactive | Non-Reactive | Reactive |
| 109-7 | Non-Reactive | Reactive | Reactive |
| 204-3 | Non-Reactive | Reactive | Reactive |

The claimed invention is:

1. An assay method for detecting an analyte in a liquid biological sample, comprising:
    a) contacting the liquid biological sample suspected of containing analytes with ligand-target conjugates in a liquid phase, wherein the ligand-target conjugates bind to at least a fraction of the analytes to form ligand-target-analyte complexes, and wherein a fraction of the analytes remain unbound to the ligand-target conjugate;
    b) contacting the unbound analyte and the ligand-target-analyte complexes with a receptor-label conjugate, to form analyte-receptor-label complexes and ligand-target-analyte-receptor-label complexes;
    c) capturing the analyte-receptor-label complexes and ligand-target-analyte-receptor-label complexes on a surface comprising immobilized capture agents, wherein:
        (i) a fraction of the immobilized capture agents are pre-complexed with ligand-target conjugates, wherein the pre-complexed ligand-target conjugates bind to the analyte-receptor-label complexes to form captured ligand-target-analyte-receptor-label complexes on the surface; and
        (ii) another fraction of the immobilized capture agents are not complexed with ligand-target conjugates and bind the ligand-target-analyte-receptor-label complexes to form captured ligand-target-analyte-receptor-label complexes on the surface; and d) detecting the ligand-target-analyte-receptor-label complexes captured on the surface.

2. The assay method of claim 1, wherein the analyte is an antibody and the target is an antigen.

3. The assay method of claim 2, wherein the analyte is an anti-HIV antibody, selected from anti-HIV-1 and anti-HIV-2, and the antigen is selected from the group consisting of HIV-1 peptide, HIV-2 peptide, rAg and mixtures thereof.

4. The assay method of claim 1, wherein the ligand is biotin.

5. The assay method of claim 1, wherein the liquid biological sample is selected from the group consisting of oral fluid, whole blood and plasma.

6. The assay method of claim 1, wherein the receptor is protein A.

7. The assay method of claim 1, wherein the label is colloidal gold.

8. The assay method of claim 1, wherein the capture agent is streptavidin.

9. The assay method of claim 3, wherein the ligand-target conjugate is selected from the group consisting of biotinylated HIV-1 peptide, biotinylated HIV-2 peptide, biotinylated rAg peptide or mixtures thereof.

10. The assay method of claim 1, wherein the assay method is performed on a lateral flow assay strip, further comprising the step of contacting the lateral flow assay strip with a developer solution, wherein, after contact, the developer solution moves across the lateral flow assay strip.

11. The assay method of claim 10, wherein the liquid biological sample is added to the developer solution.

12. The assay method of claim 10, wherein the liquid biological sample is added to a sample receiving portion of the lateral flow assay strip.

13. The assay method of claim 10, wherein the target-ligand conjugate is added to the developer solution.

14. The assay method of claim 10, wherein the target-ligand conjugate is eluted off a portion of the lateral flow assay strip downstream of the sample receiving area to bind to the analyte.

15. A lateral flow assay strip for detecting an analyte in a liquid biological sample comprising:
   a sample receiving area;
   a blocker area downstream from the sample receiving area comprising ligand-target conjugates for forming ligand-target-analyte complexes, wherein the ligand-target conjugates are specific for the analyte;
   a conjugate area downstream from the blocker area, comprising receptor-label conjugates for forming ligand-target-analyte-receptor-label complexes and analyte-receptor-label complexes, wherein the receptor-label conjugates are specific for any unbound analyte and the ligand-target-analyte complexes; and
   at least one test zone downstream from the conjugate area comprising immobilized capture agents, wherein:
      (i) a fraction of the immobilized capture agents are pre-complexed with ligand-target conjugates and capture analyte-receptor-label complexes; and
      (ii) another fraction of the immobilized capture agents are not complexed with ligand-target conjugates and capture ligand-target-analyte-receptor-label complexes.

16. The lateral flow assay strip of claim 15, wherein the analyte is an antibody and the target is an antigen.

17. The lateral flow assay strip of claim 16, wherein the analyte is an anti-Human Immunodeficiency Virus (HIV) antibody, selected from anti-HIV-1 and anti-HIV-2, and the antigen is selected from the group consisting of HIV-1 peptides, HIV-2 peptides, a recombinant antigen (rAg), and mixtures thereof,
   wherein the rAg comprises an amino acid as set forth in SEQ ID NO: 2,
   wherein the HIV-1 peptides comprise peptides derived from HIV-1 gp120, gp41, p24, or p17 proteins or combinations thereof, and
   wherein the HIV-2 peptides comprise peptides derived from HIV-2 gp120, gp41, p24, or p17 proteins or combinations thereof.

18. The lateral flow assay strip of claim 15, wherein the ligand is biotin.

19. The lateral flow assay strip of claim 15, wherein the receptor is protein A.

20. The lateral flow assay strip of claim 15, wherein the label is colloidal gold.

21. The lateral flow assay strip of claim 15, wherein the capture agent is streptavidin.

22. The lateral flow assay strip of claim 17, wherein the ligand-target conjugate is selected from the group consisting of biotinylated HIV-1 peptide, biotinylated HIV-2 peptide, biotinylated rAg peptide or mixtures thereof.

23. A kit comprising:
   a) the lateral flow assay strip of claim 15; and
   b) a developer solution.

24. The method of claim 1, wherein the analyte is selected from the group consisting of antibodies to HIV, antibodies to HPV, antibodies to HCV, antibodies to Ebola, antibodies to Dengue, antibodies to Zika, antibodies to *Helicobacter pylori*, antibodies to hepatitis, antibodies to measles, hepatitis antigens, antibodies to terponemes, antibodies to host or infections agents, cellular markers of pathology including, but not limited to, cardiolipin, lecithin, cholesterol, lipopolysaccharide and sialic acid, antibodies to mumps, antibodies to rubella, cotinine, cocaine, benzoylecgonine, benzodiazapines, tetrahydrocannabinol, nicotine, ethanol theophylline, phenytoin, acetaminophen, lithium, diazepam, nortriptyline, secobarbital, phenobarbital, theophylline, testosterone, estradiol, 17-hydroxyprogesterone, progesterone, thyroxine, thyroid stimulating hormone, follicle stimulating hormone, luteinizing hormone, transforming growth factor alpha, epidermal growth factor, insulin-like growth factors I and II, growth hormone release inhibiting factor, IGA, sex hormone binding globulin, glucose, cholesterol, caffeine, corticosteroid-binding globulin, PSA, DHEA-binding glycoprotein, and combinations thereof.

* * * * *

SEQUENCE LISTING

<160> NUMBER OF SEQ ID NOS: 2

<210> SEQ ID NO 1
<211> LENGTH: 966
<212> TYPE: DNA
<213> ORGANISM: Artificial Sequence
<220> FEATURE:
<223> OTHER INFORMATION: Synthetic

<400> SEQUENCE: 1

```
atggcgacga aggccgtgtg cgtgctgaag ggcgacggcc cagtgcaggg catcatcaat      60
ttcgagcaga aggaaagtaa tggaccagtg aaggtgtggg aagcattaa aggactgact     120 gaaggcctgc atggattcca tgttcatgag tttggagata atacagcagg ctgtaccagt     180
gcaggtcctc actttaatcc tctatccaga aaacacggtg ggccaaagga tgaagagagg     240
catgttggag acttgggcaa tgtgactgct gacaaagatg gtgtggccga tgtgtctatt     300
gaagattctg tgatctcact ctcaggagac cattgcatca ttggccgcac actggtggtc     360
catgaaaaag cagatgactt gggcaaaggt ggaaatgaag aaagtacaaa gacaggaaac     420
gctggaagtc gtttggcttg tggtgtaatt gggatcgccc aagttttccg tcctggcggt     480
ggcgatatga gagacaactg gagaagcgaa ttatacaaat acaaagtgat taagattgaa     540
ccattgggca ttgccccaac caaagcgaag cgtagagttg tgcagcgcga aaaacgtcag     600
gctagacaac tgttatctgg cattgttcaa cagcaaaata acttgctgag agctatcgaa     660
gcacagcaac atctgctgca actgactgtg tggggtatca agcagttgca agctcgcgtc     720
ctggcagtag aacgttatct gcgtgatcag caactgttag gtatttgggg ctgtagcggt     780
aaattgatct gcaccactgc cgttccgtgg aatgcgtctt ggtcaaacaa gagtttagaa     840
gatatttggg acaatatgac ctggatgcaa tgggaacgtg aaattgacaa ctacacaaac     900
acgatctaca cattattaga agaatcgcag aaccagcagg aaaagaacga acaggaatta     960
ttatag                                                              966
```

<210> SEQ ID NO 2
<211> LENGTH: 321
<212> TYPE: PRT
<213> ORGANISM: Artificial Sequence
<220> FEATURE:
<223> OTHER INFORMATION: Synthetic

<400> SEQUENCE: 2

```
Met Ala Thr Lys Ala Val Cys Val Leu Lys Gly Asp Gly Pro Val Gln
1               5                   10                  15
```

-continued

```
Gly Ile Ile Asn Phe Glu Gln Lys Glu Ser Asn Gly Pro Val Lys Val
            20                  25                  30
Trp Gly Ser Ile Lys Gly Leu Thr Glu Gly Leu His Gly Phe His Val
            35                  40                  45
His Glu Phe Gly Asp Asn Thr Ala Gly Cys Thr Ser Ala Gly Pro His
    50                  55                  60
Phe Asn Pro Leu Ser Arg Lys His Gly Pro Lys Asp Glu Glu Arg
65                  70                  75                  80
His Val Gly Asp Leu Gly Asn Val Thr Ala Asp Lys Asp Gly Val Ala
                85                  90                  95
Asp Val Ser Ile Glu Asp Ser Val Ile Ser Leu Ser Gly Asp His Cys
            100                 105                 110
Ile Ile Gly Arg Thr Leu Val Val His Glu Lys Ala Asp Asp Leu Gly
            115                 120                 125
Lys Gly Gly Asn Glu Glu Ser Thr Lys Thr Gly Asn Ala Gly Ser Arg
130                 135                 140
Leu Ala Cys Gly Val Ile Gly Ile Ala Gln Val Phe Arg Pro Gly Gly
145                 150                 155                 160
Gly Asp Met Arg Asp Asn Trp Arg Ser Glu Leu Tyr Lys Tyr Lys Val
            165                 170                 175
Ile Lys Ile Glu Pro Leu Gly Ile Ala Pro Thr Lys Ala Lys Arg Arg
            180                 185                 190
Val Val Gln Arg Glu Lys Arg Gln Ala Arg Gln Leu Leu Ser Gly Ile
            195                 200                 205
Val Gln Gln Gln Asn Asn Leu Leu Arg Ala Ile Glu Ala Gln Gln His
    210                 215                 220
Leu Leu Gln Leu Thr Val Trp Gly Ile Lys Gln Leu Gln Ala Arg Val
225                 230                 235                 240
Leu Ala Val Glu Arg Tyr Leu Arg Asp Gln Gln Leu Leu Gly Ile Trp
            245                 250                 255
Gly Cys Ser Gly Lys Leu Ile Cys Thr Thr Ala Val Pro Trp Asn Ala
            260                 265                 270
Ser Trp Ser Asn Lys Ser Leu Glu Asp Ile Trp Asp Asn Met Thr Trp
            275                 280                 285
Met Gln Trp Glu Arg Glu Ile Asp Asn Tyr Thr Asn Thr Ile Tyr Thr
    290                 295                 300
Leu Leu Glu Glu Ser Gln Asn Gln Gln Glu Lys Asn Glu Gln Glu Leu
305                 310                 315                 320
Leu
```